United States Patent [19]

Goebel et al.

[11] 4,182,713
[45] Jan. 8, 1980

[54] BENZOTRIAZOLES USEFUL AS AZO DYESTUFF INTERMEDIATES

[75] Inventors: Hermann Goebel, Leverkusen; Erich Krämer, Berg. Gladbach, both of Fed. Rep. of Germany

[73] Assignee: Bayer Aktiengesellschaft, Leverkusen, Fed. Rep. of Germany

[21] Appl. No.: 896,143

[22] Filed: Apr. 13, 1978

[30] Foreign Application Priority Data

Apr. 14, 1977 [DE] Fed. Rep. of Germany ....... 2716503

[51] Int. Cl.² .......................................... C07D 253/02
[52] U.S. Cl. ..................... 548/259; 8/1 D; 8/1 E; 544/194; 544/311
[58] Field of Search ..................................... 260/308 B

[56] References Cited

U.S. PATENT DOCUMENTS

| 3,267,113 | 8/1966 | Carboni | 260/308 |
| 3,272,891 | 9/1966 | Milionis et al. | 260/895 |
| 3,951,592 | 4/1976 | Botros | 8/41 C |

OTHER PUBLICATIONS

McOmie, J., "Protective Groups in Organic Chemistry," Plenum Press, N.Y., (1973), p. 57.

*Primary Examiner*—Donald G. Daus
*Assistant Examiner*—Lisa Jones
*Attorney, Agent, or Firm*—Sprung, Felfe, Horn, Lynch & Kramer

[57] ABSTRACT

The compound which corresponds to the formula

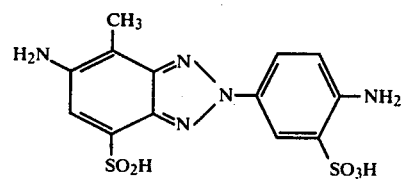

is suitable for the preparation of azo dyestuffs.

1 Claim, No Drawings

BENZOTRIAZOLES USEFUL AS AZO DYESTUFF INTERMEDIATES

The invention relates to the compound which, in the form of the free acid, corresponds to the formula

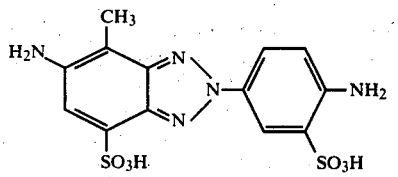

and its use for the preparation of azo dyestuffs.

The compound is obtained by diazotising the amine of the formula

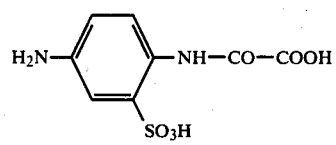

coupling the diazotisation product with 3,5-diamino-4-methyl-benzenesulphonic acid, treating the coupling product with ammonia and a copper-II salt under the influence of heat until triazolisation has ended and then splitting off the oxalic acid radical hydrolytically in an alkaline medium.

The compound according to the invention can be tetrazotised extremely readily and is therefore suitable for building up disazo and polyazo dyestuffs. Because of the different basicity of the free amino groups, the compound according to the invention can also be acylated on one side on the amino group of the benzotriazole radical and is thus suitable, for example, for the preparation of fibre-reactive azo dyestuffs.

EXAMPLE 1

29 g of the compound (II) are dissolved in 300 ml of water, 28 ml of hydrochloric acid (of °Bé strength 19.5) are added and the compound is diazotised at 0°–5° C. with 6.9 g of sodium nitrite. This solution is added to a solution of 20.2 g of 3,5-diamino-4-methylbenzenesulphonic acid in 200 ml of water, and 200 ml of 20% strength aqueous sodium acetate solution are simultaneously added. The orange-coloured solution formed is heated to 85° C., a solution of 56 g of copper sulphate in 100 ml of 25% strength aqueous ammonia is added and the mixture is heated to 85° C. for about 6 hours. Decolorisation of the solution indicates the end of triazolisation.

70 ml of sodium hydroxide solution (40% strength by volume) are then added and the solution is heated to 98° C. for one hour.

After adding kieselguhr, the insoluble constituents are filtered off, 28%, relative to the solution, of sodium chloride are added to the filtrate, the mixture is stirred for 12 hours and the precipitate is filtered off. This gives 87 to 88% (determination by tetrazotisation) of the compound (I), which is obtained in pale yellowish crystals.

EXAMPLE 2

13.8 g of p-nitroaniline are diazotised in a known manner and the diazotisation product is coupled with 32 g of H-acid in the pH range which is acid to Congo Red (solution 1). 39 g of the compound (I) are dissolved in 300 ml of water, 58 ml of hydrochloric acid (of °Bé strength 19.5) are added and the compound is tetrazotised at 0°–5° C. with 13.8 g of sodium nitrite in the form of an aqueous solution (solution 2). Solution 1 is rendered neutral, 70 g of sodium carbonate are added and solution 2 is allowed to run in. After the coupling on one side has ended, 10.8 g of m-phenylenediamine are added in the form of an aqueous solution. The completely coupled dyestuff is salted out and isolated. It dyes leather in greenish-tinged deep black shades.

EXAMPLE 3

39 g of the compound (I) are dissolved in 400 ml of water. After adding 150 ml of a 20% strength aqueous sodium acetate solution, 17 g of 2,4,6-trifluoro-5-chloropyrrimidine are added dropwise at 0°–5° C. in the course of one hour, whilst stirring well, the compound of the following structure being formed:

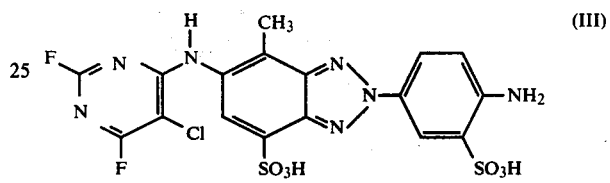

50 g of hydrochloric acid (of °Bé strength 19.5) are added, without intermediate isolation of this compound, and the compound is diazotised at 0°–5° C. with 6.9 g of sodium nitrite in the form of an aqueous solution.

43 g of N-benzoyl-H-acid are dissolved in 400 ml of water to give a neutral solution. After adding 85 g of sodium bicarbonate, the solution described above of the diazotised amine is allowed to run in at 5°–10° C. The completely coupled dyestuff is isolated in the customary manner by salting out and dyes cotton in a brilliant bluish-tinged red colour shade by dyeing methods customary for reactive dyestuffs. The dyeings are distinguished by a high degree of fixing and excellent fastness to light and wet processing.

If N-benzoyl-H-acid in the above example is replaced by other suitable coupling components, a large number of diverse reactive dyestuffs, predominantly having a brillant colour shade, can be built up. The table which follows indicates which colour shades are achieved when the diazotised amine (II) is coupled with the coupling components indicated in the column.

| Coupling components | Colour shade |
| --- | --- |
| 1-Acetylamino-8-hydroxynaphthalene-3,6-disulphonic acid | red |
| 1-Acetylamino-8-hydroxynaphthalene-4,6-disulphonic acid | red |
| 1,8-Dihydroxynaphthalene-3,6-disulphonic acid | bluish-tinged red |
| 2-Hydroxynaphthalene-6-sulphonic acid | orange |
| 2-Hydroxynaphthalene-3,6-disulphonic acid | red |
| 1-Hydroxynaphthalene-3-sulphonic acid | scarlet |
| 1-(4-40 -Sulphophenyl)-3-methylpyrazol-5-one | yellow |
| Barbituric acid | greenish-tinged yellow |
| The 1,1 Cu complex of 2,2′,4-trihydroxy-5′-sulphoazobenzene | brown |
| 1-(4-Sulphophenyl)-3-carboxypyrazol-5-one | yellow |
| 2-Acetoacetylamino-1-methoxybenzene-4- | |

| Coupling components -continued | Colour shade |
|---|---|
| sulphonic acid | yellow |

EXAMPLE 4

19 g of cyanuric chloride are dissolved in 300 ml of acetone. This solution is poured into 400 ml of water having a temperature of 0° C. The cyanuric chloride thereby precipitates in the form of a fine suspension. First 150 ml of 20% strength by volume aqueous sodium acetate solution and then a neutral solution of 39 g of the compound (I) in 300 ml of water are added to this suspension. The temperature should always be 0° C. during the condensation. The intermediate product of the following formula

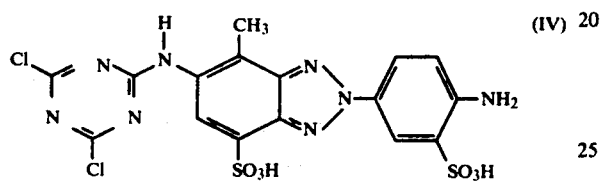 (IV)

is isolated by salting out.

The compound (IV) is stirred well in 400 ml of water and 33 ml of hydrochloric acid (of ° Bé strength 19.5) and is diazotised at 0° C. with 5 g of sodium nitrite in the form of an aqueous solution. 12.8 g of barbituric acid are dissolved in 200 ml of water with sodium hydroxide solution to give a weakly alkaline solution. After buffering to pH 7, 100 g of sodium bicarbonate are added and diazotised amine is then added to the solution. After coupling has ended, crystallisation of the dyestuff is brought to completion by added sodium chloride. The dyestuff is filtered off and dried in vacuo at 20°–25° C. The dyestuff thus prepared is yellow-orange powder which dyes cotton and wool in greenish-tinged yellow colour shades by customary dyeing methods for reactive dyestuffs.

We claim:
1. Compound which, in the form of the free acid, corresponds to the formula

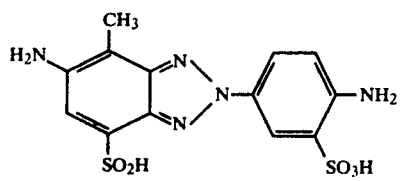

* * * * *

UNITED STATES PATENT AND TRADEMARK OFFICE
CERTIFICATE OF CORRECTION

PATENT NO. : 4,182,713
DATED : January 8, 1980
INVENTOR(S) : HERMANN GOEBEL and ERICH KRÄMER It is certified that error appears in the above-identified patent and that said Letters Patent are hereby corrected as shown below:

| Column | Line | |
|---|---|---|
| 2 | 35 | "benzoly" should be --benzoyl-- |
| 2 | 40 | "brillant" should be --brilliant-- |
| 2 | 51 | "(II)" should be --(III)-- |
| 2 | 63 | "4-40" should be --4'-- |
| 4 | 9 | insert --the-- before "coupling" |
| 4 | 26 | "$SO_2H$" should be -- $SO_3H$ --. |

Signed and Sealed this

Fifteenth Day of July 1980

[SEAL]

Attest:

SIDNEY A. DIAMOND

Attesting Officer     Commissioner of Patents and Trademarks